United States Patent
Sui et al.

(10) Patent No.: US 8,323,198 B2
(45) Date of Patent: Dec. 4, 2012

(54) SPATIAL AND TEMPORAL ALIGNMENT FOR VOLUME RENDERING IN MEDICAL DIAGNOSTIC ULTRASOUND

(75) Inventors: Lei Sui, Renton, WA (US); Arun Tirumalai, Sammamish, WA (US); Richard M. Bennett, Half Moon Bay, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1043 days.

(21) Appl. No.: 11/699,681

(22) Filed: Jan. 29, 2007

(65) Prior Publication Data

US 2008/0300486 A1 Dec. 4, 2008

(51) Int. Cl.
- *A61B 8/00* (2006.01)
- *A61B 5/055* (2006.01)
- *G06K 9/00* (2006.01)

(52) U.S. Cl. ......... 600/444; 600/407; 600/443; 382/128
(58) Field of Classification Search .................. None
See application file for complete search history.

(56) References Cited

U.S. PATENT DOCUMENTS

| | | | |
|---|---|---|---|
| 6,056,691 A * | 5/2000 | Urbano et al. | 600/443 |
| 6,086,537 A * | 7/2000 | Urbano et al. | 600/443 |
| 6,558,325 B1 | 5/2003 | Pang et al. | |
| 6,673,017 B1 | 1/2004 | Jackson | |
| 6,780,152 B2 | 8/2004 | Ustuner et al. | |
| 6,980,844 B2 | 12/2005 | Schoisswohl | |
| 2004/0006266 A1 | 1/2004 | Ustuner et al. | |
| 2005/0049502 A1 | 3/2005 | Schoisswoh | |
| 2005/0203395 A1 | 9/2005 | Sui et al. | |
| 2005/0288585 A1 | 12/2005 | Zamboglu et al. | |
| 2006/0241457 A1 | 10/2006 | Nadadur et al. | |

OTHER PUBLICATIONS

PCT International Search Report, PCT Article 18 and Rules 43 and 44, 3 pages total, date of the actual completion of the International Search Jan. 10, 2008, date of mailing of the International Search Report Jan. 25, 2008.

* cited by examiner

*Primary Examiner* — Long V. Le
*Assistant Examiner* — Angela M Hoffa

(57) ABSTRACT

Ultrasound data is aligned spatially and temporally for volume rendering of a fetal heart or other cyclically moving object. A sequence of ultrasound data is obtained for each of a plurality of planes, such as acquiring data representing each plane over one or more cycles. The different planes are scanned sequentially in a step mode acquisition. The data is aligned temporally and spatially to create data representing volumes at different times throughout the cycle. The alignment uses similarity of the ultrasound data in time and space.

17 Claims, 2 Drawing Sheets

SPATIAL AND TEMPORAL ALIGNMENT FOR VOLUME RENDERING IN MEDICAL DIAGNOSTIC ULTRASOUND

BACKGROUND

The present invention relates to volume scanning. In particular, medical diagnostic ultrasound data representing a cyclically moving objection is aligned spatially and temporally for volume rendering. The alignment creates data representing a volume at different times.

The heart of a patient may be imaged with ultrasound. The images may be three-dimensional representations displayed as a sequence. Since the heart changes shape, size, and/or position during the heart cycle, the sequence shows the heart at different phases during the heart cycle.

The data for volume imaging is acquired at different portions of the heart cycle. The heart phase associated with acquired data is used to align the data temporally. Data associated with different spatial locations at a same portion of the heart phase are grouped to form a volume.

The heart phase is determined using ECG triggering. The ECG reading identifies the heart phase associated with each acquisition. However, ECG triggering uses a separate ECG sensor or leads, leading to inconvenience. ECG may not be available for fetal hearts.

Cyclical timing may be determined from ultrasound data. One technique for volume scanning a moving object, such as the heart, uses variation in B-mode intensity or frequency analysis of the data to determine the heart cycle. The scan positions continually change during acquisition. Data is collected for different portions of the heart cycle. The coordination between cycle phase and spatial position may be difficult. Insufficient data may be accumulated for representing complete volumes at different phases of the heart cycle.

BRIEF SUMMARY

By way of introduction, the preferred embodiments described below include methods, instructions, and systems for spatial and temporal alignment for volume rendering. A sequence of ultrasound data is obtained for each plane, such as acquiring data representing the plane over one or more cycles. The different planes are scanned sequentially. The data is aligned temporally and spatially to create data representing volumes at different times throughout the cycle. The alignment uses similarity of a sequence of ultrasound data.

In a first aspect, a method is provided for spatial and temporal alignment for volume rendering. First and second pluralities of frames of ultrasound data are acquired for first and second different scan planes, respectively. The second plurality is acquired after the first plurality. First and second cycles are identified as a function of time from the ultrasound data for each scan plane respectively. A phase shift between the first and second pluralities of frames is determined. First and second volumes are formed from the first and second pluralities of frames. The forming is a function of the phase shift and the first and second cycles. The first volume is formed from ultrasound data representing a first cyclic phase, and the second volume is formed from ultrasound data representing a second cyclic phase.

In a second aspect, a system is provided for spatial and temporal alignment for volume rendering. A transducer and beamformer are operable to scan with ultrasound a region with a cyclical object. The transducer is operable to scan in a step mode such that a plurality of scans of a same plane is performed in each step and each step is associated with a different plane. A processor is operable to determine spatial similarity of the plurality of scans of the same plane, operable to determine a temporal similarity of the scans of different planes as a function of the spatial similarity, and operable to temporally and spatially align the scans into volumes.

In a third aspect, a computer readable storage medium has stored therein data representing instructions executable by a programmed processor for spatial and temporal alignment for volume rendering. The storage medium includes instructions for collecting a sequence of images at each of a plurality of different imaging planes, identifying, in each sequence, images associated with a same phase of a cycle, temporally aligning the sequences of images, and forming volumes each representing a different phase of the cycle from the sequences.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A periodically moving object is scanned with step mode at multiple positions. At each position, data is collected over more than a cycle. For each plane, a sequence is acquired. The collection steps to another plane after acquiring a sequence for the current plane. The sequence is acquired over one or more cycles. Step-mode volume collection is provided for spatial and temporal similarity application. Heart or cycle-rate in each sequence is estimated using the similarity of data acquired at the corresponding imaging plane. The length of the motion period is estimated at multiple positions or for each sequence. Event durations (heartbeats) are estimated individually rather than formulating a single estimate of duration and applying the estimate to all events. The most likely estimation of the cycle length is used to reconstruct the volume of the moving object. Cross-similarity between imaging planes from the step mode finds the cycle phase shift due to probe motion or other delays in shifting between planes. The number of images in a cycle from each sequence is normalized to limit uneven periodic motion.

Step mode acquisition and determining similarity over time for a plane and between sequences may provide reliable fetal heart rate estimation. Improved quality of spatial data reconstruction may also be provided.

Improved feedback to the user regarding the quality of data being acquired 4D fetal heart volume motion may be provided using step mode acquisition. A statistical measure, such as variance of the cycle estimation, is used as a quality indicator. During acquisition, the standard deviation of heart rate estimation indicates the data quality. Ongoing heart/rate quality display warns the user about current data quality/consistence.

Figure 1:
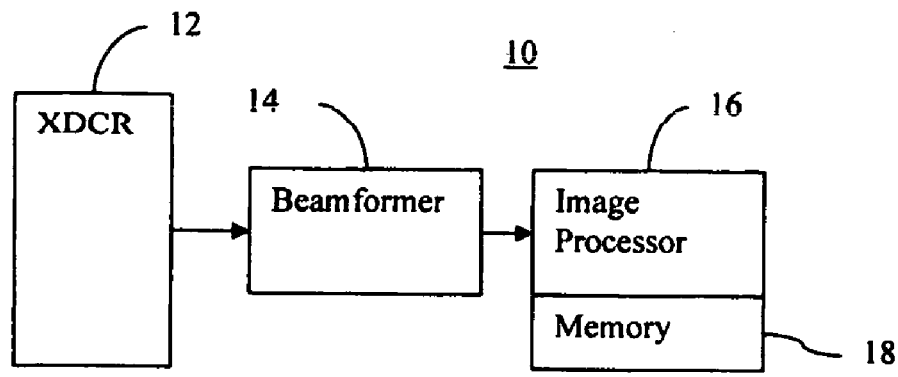
FIG. 1 is a block diagram of one embodiment of a system for spatial and temporal alignment for volume rendering.

FIG. 1 shows a system 10 for spatial and temporal alignment for volume rendering. In one embodiment, the system 10 is a medical diagnostic ultrasound system. The system 10 is a system for scanning, a workstation or personal computer. The system 10 includes a transducer 12, a beamformer 14, an image processor 16, and memory 18. Additional, different, or fewer components may be provided. In other embodiments, the system 10 is a different type of medical system and associated components, such as magnetic resonance, positron emission, computed tomography or x-ray imaging system. The alignment is for any cyclically moving object, such as the heart, lungs, stomach, diaphragm, or vessels.

The transducer 12 is an array of elements, such as piezoelectric or capacitive elements. The array is a one-dimensional or multi-dimensional distribution of elements. For example, the transducer 12 is a two-dimensional array for scanning a volume electronically. As another example, the transducer 12 is a wobbler transducer array for scanning in one dimension electronically and in another dimension mechanically. Other now known or later developed transducers 12 for mechanical and/or electrical steering of different planes may be provided. For example, a user may move the transducer 12 manually or robotically to a new location for each plane.

The beamformer 14 is a transmit beamformer, receive beamformer, combinations thereof, or other now known or later developed device for scanning a region with the transducer 12. In one embodiment, the beamformer 14 includes transmitters or waveform generators for generating electrical waveforms for each element of a transmit aperture. The electrical waveforms are relatively weighted and delayed to form an acoustic beam. Converging, diverging or planar beams may be used. The beam former 14 may include receive beamformers, such as delays, phase rotators, amplifiers, and/or adders for relatively delaying and summing received signals to form one or more receive beams with dynamic focusing. Alternatively, the beamformer 14 includes a processor for Fourier or other analysis of received signals to generate samples representing different spatial locations of the scanned region.

The beamformer 14 is operable to scan with ultrasound a region with a cyclical object. By generating transmit waveforms and forming beams with received signals, the beamformer 14 scans a planar region. Any scan format may be used, such as linear, sector, or Vector®. For a given planar region, the scan may be repeated. By repeating the scan, a sequence of frames data or images is obtained. The images or frames of ultrasound data correspond to beamformed, detected (e.g., B-mode, velocity, energy, power, variance, harmonic, contrast agent, or combinations thereof), and/or scan converted data. Each image or frame represents the entire two-dimensional scanned area, but may only represent sub-areas. The sequence at each plane covers at least one motion cycle of the imaged object, but may last for only a portion of the cycle. In the application of fetal heart imaging whose rate is usually between 110 to 120 beats/minute, the imaging time at each plane may be about 0.6 seconds.

The beamformer 14 and transducer 12 are operable to scan in a step mode. For example, a wobbler transducer mechanically shifts an array to a new position. A sequence of images is acquired before shifting to another position. As another example, different planes are sequentially scanned with electronic focusing. For each plane, a sequence of images is acquired before stepping to another plane. A plurality of scans of a same plane is performed in each step, and each step is associated with a different plane. When imaging volumes of a periodically-moving object such as a heart, step mode is used to scan a sequence of images at multiple imaging planes. Each step corresponds to obtaining data over one cycle or a portion of a cycle of the cyclical object. Interleaving of portions of scans (spatial and/or temporal) for different planes may be provided.

The processor 16 is a general processor, control processor, application-specific integrated circuit, field-programmable gate array, digital circuit, analog circuit, digital signal processor, combinations thereof, or other now known or later developed device for spatial and temporal alignment of acquired data. The processor 16 is a single device or group of devices. For example, the processor 16 includes separate processors operating in parallel or sequence. As another example, the processor 16 includes a network of devices for distributed processing in parallel or sequence. In one embodiment, the processor 16 includes a three-dimensional image rendering processor, such as a graphics processing unit, graphics card, or other device for rendering.

The processor 16 is operable to determine spatial similarity of the plurality of scans of each plane. The similarity provides cycle information. One or more images are selected from a sequence for a plane. The image or images with a maximum or sufficient similarity within the sequence are identified. The search may be based or limited by expected cycle periods, such as first searching frames of data acquired about one expected cycle previous or after the image or images. The similarity is determined by correlation, such as cross correlation or minimum sum of absolute differences. Alternatively, intensity variation through the sequence may be used to indicate similarity between frames of data, such as disclosed in U.S. Pat. No. 6,980,844, the disclosure of which is incorporated herein by reference. Mapping intensity as a function of time indicates the cycle, including peak or minimum intensity points. The resulting waveform indicates cycle length and other cycle characteristics. As another alternative, a Fourier or other frequency analysis of the ultrasound data is used to indicate similarity. In another embodiment, data is compressed or reduced by projection along one or two dimensions. The location associated with maximum variation is identified. The data associated with the location over time is used to identify the cycle. For example, one of the embodiments disclosed in U.S. Published Application No. 2006/0241457, the disclosure of which is incorporated herein by reference, is used to indicate similarity and the associated cycle. The similar frames of data represent repetition of the cycle.

Figure 2:
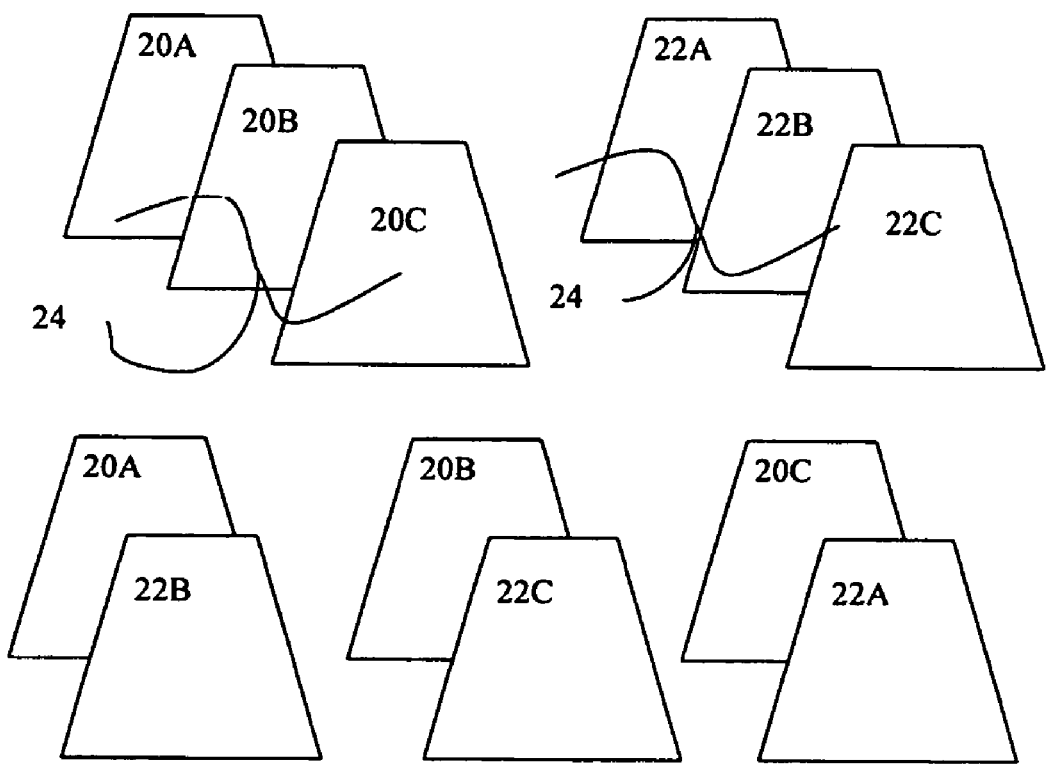
FIG. 2 is a graphical representation showing sequences for different planes temporally and spatially aligned to form volumes.

In one example shown in FIG. 2, two sequences 20 and 22 associated with two different planes are acquired. Each sequence 20, 22 includes three frames of data A-C. In actual use, a larger number of sequences and frames within each sequence may be provided. A cyclical waveform 24 is shown for each sequence 20, 22. For the first sequence 20, the first frame 20A of data is at a cyclical minimum. For the second sequence 22, the second frame 22B is at the cyclical minimum. The second frame 20B of the first sequence 20 and the third frame 22C of the second sequence 22 are at a zero crossing. The third frame 20C of the first sequence 20 and the first frame 22A of the second sequence 22 are at a cyclical maximum.

The processor 16 is operable to determine a temporal similarity of the scans of different planes as a function of the spatial similarity. The spatial similarity provides cycle information for each sequence. By comparing the cycle information, the temporal relationship between sequences is determined. The phase of one sequence is determined relative to another sequence. Cycle waveforms for the different sequences are shifted relative to each other to identify a phase shift in time with the highest or sufficient correlation. Alternatively, ultrasound data associated with one time in one sequence is matched to ultrasound data from another sequence. The frame of data in the other sequence with the greatest or sufficient similarity corresponds to the same phase in the cycle.

Based on the similarity for one or more matches, the frames of data from the different sequences are temporally aligned. Since each sequence is associated with a different plane, the spatial relationship is also aligned. The mechanical or electrical shift between planes is measured, known or calculated.

Frames of data associated with a same phase are identified for forming a volume. The frames represent different two-dimensional regions of the volume. In the example of FIG. 2, frames 20A and 22B of data represent different spatial regions of a first volume at one time in the cycle. Frames 20B and 22C of data represent different spatial regions of a second volume (same region) at another time relative to the cycle. Frames 20C and 22A of data represent different spatial regions of a third volume (same region) at yet another time relative to the cycle. Each of the volumes represents a same region, but at a different portion of the physiological cycle.

Alignment is performed conceptually, such as by labeling the frames of data, or physically, such as loading frames of data into a memory as separate volumes. The frames of data may be labeled or recorded for rendering from memory. Alternatively, the frames are grouped together in memory for rendering.

The number of frames and associated scans are normalized. Due to cycle variation, a different number of frames of data may be provided in one sequence as compared to another sequence. Frames of data corresponding to the missing phase may be selected from other cycles within a same sequence. Alternatively, interpolation and/or extrapolation may be used within the sequence to add missing frames of data. In other embodiments, the ultrasound data is decimated to match the number of frames of data. Additionally or alternatively, weighted interpolation may be used to align temporally data offset slightly in time relative to the cycle. In other embodiments, volumes are generated without adjustment or matching a number of frames.

The volumes represent the scanned region at different portions of the cycle for a sequence of volume data. The data is formatted in an acquisition format or interpolated to a three-dimensional grid as voxel data. The volumes are rendered to generate a sequence of three-dimensional representations from the volumes. The rendering is of any now known or later developed rendering, such as projection, surface, or alpha blending. By displaying the resulting sequence of three-dimensional representations, the scanned region is shown moving throughout the cycle.

The processor 16 optionally indicates the quality of acquired or collected data. The quality is indicated visually and/or audibly. Any quality parameter may be used. For example, a standard deviation of the temporal similarity is determined. The length of each cycle is determined as a sequence of frames of data is collected. By comparing the length to one or more, such as an average or median cycle length, an indication of the quality of data is obtained. If the fetus or scanned object moves, a resulting offset of the cycle length may result. The standard deviation and/or similarity of other characteristics may be used, such as determining a standard deviation as a function of time throughout a cycle.

The memory 18 is a cache, buffer, RAM, removable media, hard drive or other computer-readable storage media. Computer-readable storage media include various types of volatile and non-volatile storage media. The functions, acts or tasks illustrated in the figures or described herein are performed by the processor 16 executing instructions stored in or on the computer-readable storage media of the memory 18. The functions, acts or tasks are independent of the particular type of instructions set, storage media, processor or processing strategy and may be performed by software, hardware, integrated circuits, firmware, microcode and the like, operating alone or in combination. Likewise, processing strategies may include multi-processing, multi-tasking, parallel processing and the like. In one embodiment, the instructions are stored on a removable media device for reading by a medical diagnostic imaging system. The imaging system uploads the instructions for performing the acts discussed herein. In another embodiment, the instructions are stored in a remote location for transfer through a computer network or over telephone lines to an imaging system or workstation. In yet other embodiments, the instructions are stored within the imaging system or workstation.

The memory 18 alternatively or additionally stores the collected ultrasound data and/or spatial or temporal information.

Figure 3:
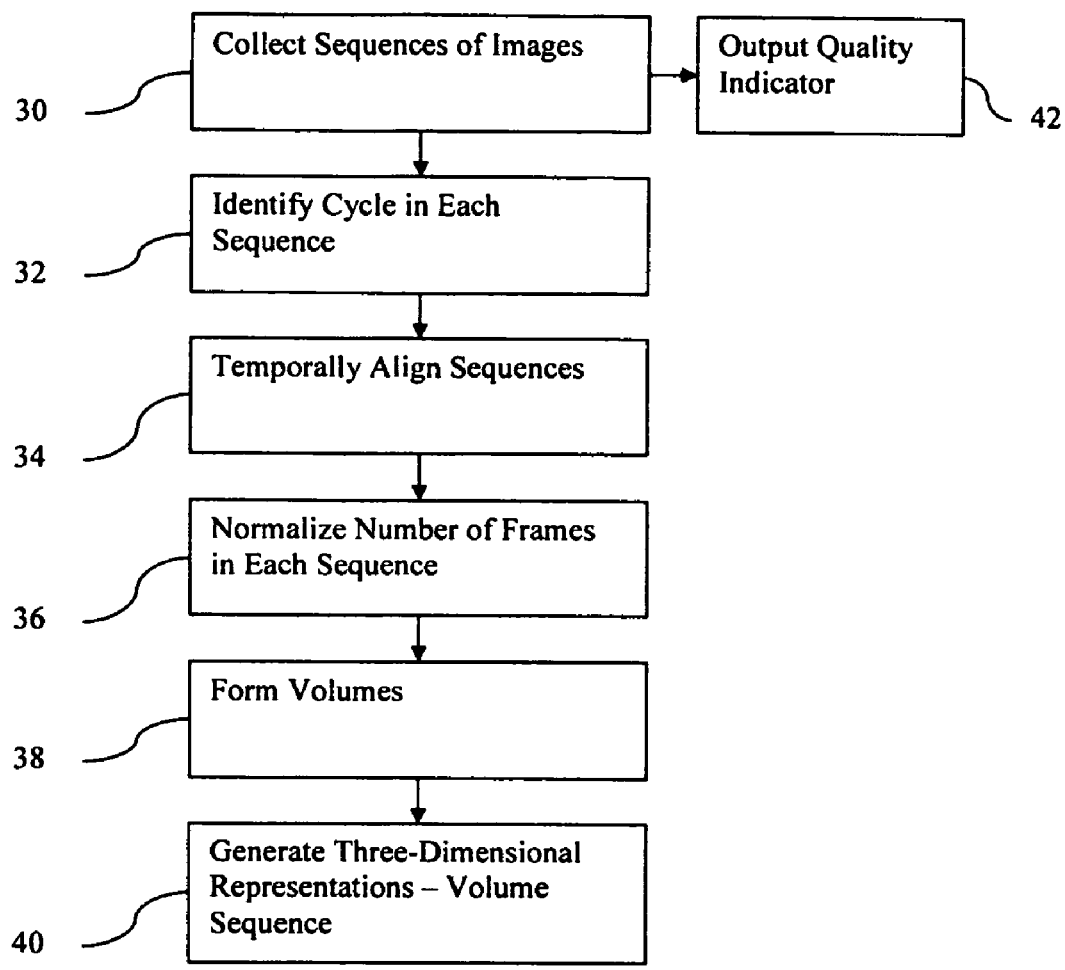
FIG. 3 is a flowchart diagram of one embodiment of a method for spatial and temporal alignment for volume rendering.

FIG. 3 shows a method for spatial and temporal alignment for volume rendering. The method is implemented on the system 10 of FIG. 1 or a different system. Additional, different or fewer acts may be provided. For example, acts 32, 34, and 38 are provided without other acts.

In act 30, a sequence of images is collected at each of a plurality of different imaging planes. The images of each sequence represent the scanned plane over at least one motion cycle of a cyclical object, such as the fetal heart. For example, each sequence is acquired over about 0.4-0.8 seconds (e.g., about 0.6 seconds). Any number of frames may be acquired during the period. Longer or shorter periods may be used.

One plurality of frames of ultrasound data are acquired for a first scan plane. Another plurality of frames of ultrasound data are acquired for another scan plane. Other sequences may be acquired for other planes. Each sequence has the same or different characteristics, such as scan pattern, frame rate, duration, or type of imaging.

In act 32, one or more cycles are identified in each sequence. The cycles for each sequence are identified independent of cycles in other sequences. The cycles are identified as a function of time from the ultrasound data. Frames of data for each scan plane are processed to identify the cycle of the object being scanned. The interval of motion period is estimated using similarity within each sequence. The first N frames in a sequence are used to find the maximal similarity in the rest of sequence. For example, N is selected to be a number of frames acquired in about 40 milliseconds (e.g., the iso volume contraction time). Each frame N is matched, or an average of the N frames is matched to other frames in the sequence to find the similarity. A threshold may be used to limit searching, such as threshold set to identify more likely a single cycle. Other similarities may be used, such as intensity variation. The time between the frames with the most similarity is the motion period. By using a moving window, other phases of multiple cycles may be matched.

The similarity is determined automatically, such as without user input. User input or confirmation may be provided.

A sequence may include multiple cycles. One cycle is selected, such as the first or a later complete cycle. Alternatively, statistical methods, such as mean or votes, may be used for an overall cycle estimate for the sequence. Frames of data from different periods may be combined to form a sequence for a single cycle.

By determining a cycle for each sequence, images or data associated with a same phase of the cycle are identified in each sequence. Cycles of each sequence represent a different period of the cycle of the scanned object, such as a fetal heart cycle.

In act 34, the sequences of images are temporally aligned. The phase shift between or relative to different sequences is determined. The sequences are shifted to provide frames of data representing different planes at a same phase of the cycle. Since sequences are available, different groups of data from different phases are provided.

The phase shift is determined by a similarity between the cycles and/or sequences. The phase shift between sequences of different imaging planes can be estimated by cross-similarity. The cross-similarity between two sequences from neighboring planes indicates the phase shift. A waveform representing the cycles of the sequence or data matching is used to determine the phase shift. The phase shifts for aligning the various sequences to a same cycle are determined. The overall cycle is pre-determined, computed from a plurality of cycles (e.g., an average or weighted average), selected from one cycle (e.g., a cycle determined for a more centrally located plane), or other source.

In act 36, a number of images is normalized for each sequence. One sequence is selected, such as a sequence representing a more centrally positioned scan plane. Alternatively, a predetermined number of frames or the sequence with the most frames in a given cycle is used. The number of frames of data and/or frames representing specific phases of the cycle in the other sequences is set to be the same. Decimation, interpolation (e.g., weighted averaging), nearest neighbor, and/or extrapolation may be used. Uneven periodic motion is solved by normalizing the number of images in a cycle. The cycles from the different sequences are normalized to the longest cycle frames by interpolation or extrapolation.

In act 38, volumes are formed. The sequences of images are aligned across the imaging planes for a synchronized playback. Each volume has a same number of frames of data and corresponding spatial resolution. Alternatively, one or more volumes may not include a frame of data from one or more sequences.

Each volume includes frames of data from different sequences, but a same or similar phase of the cycle. Each volume represents a different phase of the cycle. The phase shift is used to identify frames of data from different sequences and scan planes associated with a same or similar portion of the cycle. The cycle information adjusted by the relative phase shift allows identification and selection of frames of data. The temporally and spatially aligned frames of data are used to form a sequence of volumes. Frames of data are grouped together for rendering from frames representing a same cyclic phase and different spatial locations or planes.

In act 40, a sequence of three-dimensional representations is generated from the volumes. The volumes are interpolated to a three-dimensional grid. Alternatively, the rendering is performed from data in an acquisition or other format. Ray casting or other rendering techniques may be used. The data may be classified or transformed, such as for opacity or color. More than one type of data may be used, such as having different or combined volumes for different types of ultrasound data (e.g., B-mode and Doppler flow mode data).

By displaying the sequence of three-dimensional representations, the change in shape, size, and/or position of a cyclic organ may be shown. The change is shown over one or more cycles, but may be for only a portion of a cycle. One or more volumes associated with a specific phase, such end diastole or systole, may be used to generate specific three-dimensional representations without displaying the sequence. By aligning the frames of data spatially and temporally, one or more desired volumes are available for imaging or analysis.

The entire process may be automated. For example, the user initiates the process and positions the transducer. The step mode acquisition followed by rendering occurs without further input. If the user does not quit during scanning, the reconstructed 4D volumes are displayed in a renderer once the collection is finished. Alternatively, the user controls or provides input during the process.

In act 42, the quality of data being acquired or previously acquired may be indicated to the user. A shift of the transducer relative to the patient or of the imaged object may result in poor quality data. For example, a fetus may shift. The quality is indicated during acquisition so that the user may start over if there is a problem while avoiding or limiting wasted time or erroneous results.

Any quality parameter may be used. In one embodiment, a standard deviation of a temporal similarity between sequences indicates quality. The cycle length of each new sequence is compared to an average or other cycle lengths. The standard deviation of the cycle lengths indicates quality. The standard deviation of the multiple estimates can be treated as an indication of evenness of cycles during the scan. The deviation of other characteristics may be used, such as time between maximum and minimum. In other embodiments, cycle length or other cycle characteristic for a sequence may be compared to a predetermined or other sequence weighted threshold. The quality parameter is based on a single cycle, an average cycle, or combinations of cycles determined in a sequence.

A quality indicator is output to the user. During the data acquisition, the heart rate or cycle is estimated plane-by-plane. A progress indicator and a quality indicator indicate to the user the ongoing scanning status. The quality indicator can be color-coded or text-based. For example, a warning and/or satisfactory indication is displayed. Non-binary indicators may be used, such as outputting a value for the quality parameter.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for spatial and temporal alignment for volume rendering, the method comprising:
   acquiring a first plurality of frames of first ultrasound data for a first scan plane;
   acquiring, after the first plurality, a second plurality of frames of second ultrasound data for a second scan plane different than the first scan plane;
   identifying, with a processor, a first cycle as a function of time from the first ultrasound data for the first scan plane, the identifying of the first cycle being independent of any identification of other cycles including a second cycle, a first waveform representing the first cycle;

identifying, with the processor, the second cycle as a function of time from the second ultrasound data for the second scan plane, the identifying of the second cycle being independent of the identification of the other cycles including the first cycle, a second waveform representing the second cycle;

determining a phase shift between the first and second cycles, the determining being by shifting the first waveform representing the first cycle relative to the second waveform representing the second cycle, the phase shift being a function of correlation for different relative shifted positions of the first and second waveforms;

forming first and second volumes from the first and second pluralities of frames, the forming being a function of the phase shift and the first and second cycles, the first volume formed from the first and second ultrasound data representing a first cyclic phase and the second volume formed from the first and second ultrasound data representing a second cyclic phase;

displaying a sequence of three-dimensional representations of a cyclic organ from the first and second volumes.

2. The method of claim 1 further comprising:
determining a standard deviation of the second cycle relative to the first cycle; and
outputting, on a display, a quality indicator as a function of the standard deviation.

3. The method of claim 1 further comprising:
normalizing a number of frames for the first and second pluralities.

4. The method of claim 1 wherein the acquiring acts comprise collecting sequences, each sequence having a duration of at least one motion cycle.

5. The method of claim 1 wherein the identifying acts comprise identifying a maximum similarity within a threshold time.

6. The method of claim 1 wherein determining the phase shift comprises computing a similarity between the first and second cycles.

7. The method of claim 1 wherein forming comprises temporally aligning the first and second plurality of frames as a function of the phase shift and grouping frames associated with a same or similar phase, the first and second cyclic phases being different.

8. The method of claim 1 wherein the acts of acquiring comprises acquiring ultrasound data representing a fetal heart, wherein the first and second cycles are different periods of a fetal heart cycle of the fetal heart, and wherein the first and second volumes represent the fetal heart at different times in the fetal heart cycle.

9. A system for spatial and temporal alignment for volume rendering, the system comprising:
a transducer and beamformer configured to scan a region with a cyclical object with ultrasound, the beamformer configured to scan in a step mode where a plurality of scans of a same plane are performed in each step, each step associated with a different plane; and
a processor configured to determine spatial similarity between scans of the plurality of scans of the same plane, configured to extract cycle information from the spatial similarity, configured to determine a temporal similarity of the scans of different planes as a function of the cycle information, the temporal similarity determined by shifting the cycle information, and configured to temporally and spatially align the scans of the different planes into volumes.

10. The system of claim 9 wherein the transducer comprises a wobbler transducer.

11. The system of claim 9 wherein the processor is configured to generate a sequence of three-dimensional representations from the volumes.

12. The system of claim 9 wherein the processor is configured to determine a standard deviation of the temporal similarity, and output, on a display, a quality indicator as a function of the standard deviation.

13. The system of claim 9 wherein the processor is configured to normalize a number of scans for each step.

14. The system of claim 9 wherein each step corresponds to over one cycle of the cyclical object.

15. In a non-transitory computer readable storage medium having stored therein data representing instructions executable by a programmed processor for temporal alignment for volume rendering, the storage medium comprising instructions for:
collecting first and second sequences of images at first and second different imaging planes, respectively, wherein each of the first and second sequences correspond to images representing over one cycle of a cyclical object;
identifying, in each of the first and second sequences, images associated with a same phase of a cycle;
temporally aligning the first and second sequences of images based on the identified phases;
normalizing a number of images for each of the temporally aligned first and second sequences, the normalizing comprising setting the number of images to be the same in each of the first and second sequences; and
forming volumes each representing a different phase of the cycle from the first and second sequences, the volumes formed with the images output from the normalizing.

16. The non-transitory computer readable storage medium of claim 15 further comprising:
generating a sequence of three-dimensional representations from the volumes.

17. The non-transitory computer readable storage medium of claim 15 further comprising:
determining a standard deviation of a temporal similarity between the first and second sequences; and
outputting, on a display, a quality indicator as a function of the standard deviation.

* * * * *